(12) United States Patent
Vareberg et al.

(10) Patent No.: US 11,965,868 B2
(45) Date of Patent: Apr. 23, 2024

(54) GAS DETECTION DEVICE AND METHOD

(71) Applicant: Blue Rock Solutions, LLC, Fargo, ND (US)

(72) Inventors: Troy D. Vareberg, Fargo, ND (US); Emmy L. Vareberg, Fargo, ND (US)

(73) Assignee: Blue Rock Solutions, LLC, Fargo, ND (US)

( * ) Notice: Subject to any disclaimer, the term of this patent is extended or adjusted under 35 U.S.C. 154(b) by 120 days.

(21) Appl. No.: 17/714,228

(22) Filed: Apr. 6, 2022

(65) Prior Publication Data

US 2022/0326206 A1     Oct. 13, 2022

Related U.S. Application Data

(60) Provisional application No. 63/258,046, filed on Apr. 7, 2021.

(51) Int. Cl.
   *G01N 33/00*     (2006.01)

(52) U.S. Cl.
   CPC ..... *G01N 33/0063* (2013.01); *G01N 33/0073* (2013.01)

(58) Field of Classification Search
   USPC .......................................................... 73/46
   See application file for complete search history.

(56) References Cited

U.S. PATENT DOCUMENTS

| | | | |
|---|---|---|---|
| 4,601,194 A * | 7/1986 | Miller | E21B 47/117 73/40.7 |
| 9,296,530 B2 * | 3/2016 | Cockerham | B65D 90/105 |
| 10,429,213 B1 | 10/2019 | Golden et al. | |
| 10,816,432 B2 | 10/2020 | Tinaphong et al. | |
| 2005/0166666 A1 | 8/2005 | Tsukagoshi | |
| 2007/0289635 A1 | 12/2007 | Ghazarian et al. | |
| 2012/0018014 A1* | 1/2012 | Fernandes | F16L 23/006 137/561 A |
| 2014/0354426 A1* | 12/2014 | Luybyanitsky | G01M 3/00 340/539.26 |
| 2014/0357216 A1* | 12/2014 | Armitage | H04W 4/90 455/404.2 |
| 2021/0140844 A1 | 5/2021 | Suk et al. | |
| 2021/0188538 A1* | 6/2021 | Stroder | B65D 90/10 |
| 2021/0362944 A1* | 11/2021 | Collins | E05D 13/14 |

FOREIGN PATENT DOCUMENTS

| | | |
|---|---|---|
| EP | 2208037 B1 | 1/2017 |
| WO | 2015072745 A | 5/2015 |
| WO | 2020007428 A1 | 1/2020 |

OTHER PUBLICATIONS

McClelland, C, "IoT Connectivity 101. Here's Everything You Need to Know About IoT Connectivity", IoT for All, Feb. 13, 2018, pp. 1-4.*

* cited by examiner

*Primary Examiner* — Daniel S Larkin
(74) *Attorney, Agent, or Firm* — Danielson Legal LLC

(57) ABSTRACT

Gas detection methods, systems, and devices. The gas detection device includes a housing portion configured with at least one gas sensor, one or more processors executing instructions stored on memory to process data from the at least one gas sensor, and a communication device configured to transmit a signal regarding the processed data. The gas detection device further includes a connection component to operably position the housing portion with respect to a structure to enable the at least one gas sensor to detect a gas emitting from the structure.

16 Claims, 8 Drawing Sheets

GAS DETECTION DEVICE AND METHOD

CROSS REFERENCE TO RELATED APPLICATIONS

The present application claims the benefit of and priority to U.S. provisional application No. 63/258,046, filed on Apr. 7, 2021, the content of which is hereby incorporated by reference as if set forth in its entirety herein.

TECHNICAL FIELD

Embodiments described herein generally relate to sensor devices and methods and, more particularly but not exclusively, to sensor devices and methods for gas detection.

BACKGROUND

Regulations require facilities such as those in the energy sector to comply with various protocols. Facilities associated with oil, for example, contain a mixture of wells, pneumatic controllers or valves, storage vessels, and natural gas collection components. Complying with regulations requires inspecting these components or locations, documenting the inspection, and submitting documentation of the inspection.

Existing techniques for complying with these regulations involve manually monitoring the above locations or components. This requires personnel to manually take readings at the above locations or components to detect any emissions therefrom. After a site is surveyed, reports are created and submitted to the Environmental Protection Agency (EPA). If emissions are detected, steps are taken to remedy the situation such as by fixing leaks. This inspection-and-reporting process is time consuming and resource intensive.

Using infrared gas detection cameras to detect gas leaks has recently been proposed. Although this takes less time than the manual inspection process outlined above, the required cameras are expensive at approximately $80,000 per camera.

A need exists, therefore, for devices and methods that overcome the disadvantages of existing monitoring techniques.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a gas detection device. The gas detection device includes a housing portion configured with at least one gas sensor, one or more processors executing instructions stored on memory to process data from the at least one gas sensor, and a communication device configured to transmit a signal regarding the processed data; and a connection component to operably position the housing portion with respect to a structure to enable the at least one gas sensor to detect a gas emitting from the structure.

In some embodiments, the one or more processors are configured to periodically activate the at least one gas sensor to detect the gas emitting from the structure. In some embodiments, the one or more processors are configured to periodically activate the at least one gas sensor in accordance with a schedule.

In some embodiments, the structure is a thief hatch including a cover portion, a seal, and an interstitial space between the cover portion and the seal, and the connection component is configured to be operably connected with the cover portion to position the at least one gas sensor in the interstitial space. In some embodiments, the gas detection device further includes a position detection sensor to detect the thief hatch is open, and the transmitted signal indicates the thief hatch is open.

In some embodiments, the transmitted signal includes at least one of location data pertaining to the location of the detected gas, timing data regarding the time of the detection, or quantity of the gas detected.

In some embodiments, the gas detection device further includes a cover portion configured to receive the connection component and a mounting collar configured to removably attach to the structure. In some embodiments, the structure is a valve or a joint.

In some embodiments, the gas detection device further includes a position detection sensor to detect position of the structure.

In some embodiments, the signal is transmitted over a narrow bandwidth Internet-of-Things (IoT) connection.

In some embodiments, the gas detection device further includes a location detection device to gather data regarding location of the gas detection device.

According to another aspect, embodiments relate to a gas detection system. The system includes a gas detection device in accordance with the gas detection device described above located at a first site, a first communications module positioned at the first site and configured to communicate with the first gas detection device, and a remote monitoring system configured to receive data regarding the first gas detection device from the first communications module and issue instructions regarding the first gas detection device to the first communications module.

In some embodiments, the system further includes a second gas detection device in accordance with the gas detection device described above located at a second site; a second communications module positioned at the second site and configured to communicate with the second gas detection device; and the remote monitoring system is further configured to receive data regarding the second gas detection device from the second communications module and issue instructions regarding the second gas detection device to the second communications module.

According to yet another aspect, embodiments relate to a method for detecting gas. The method includes operably positioning a gas detection device in accordance with the gas detection device described above with respect to a structure, and enabling the gas detection device to detect a gas emitting from the structure.

In some embodiments, the method further includes receiving a signal from the gas detection device indicating the gas detection device has detected gas. In some embodiments, the received signal includes at least one of location data pertaining to the location of the detected gas, timing data regarding the time of the gas detection, or quantity of the gas detected. In some embodiments, the signal is transmitted over a narrow bandwidth Internet-of-Things (IoT) connection.

In some embodiments, the method further includes activating the gas detection device in accordance with a schedule.

In some embodiments, the structure is a thief hatch including a cover portion, a seal, and an interstitial space between the cover portion and the seal, wherein operably positioning the gas detection device includes connecting the gas detection device to the cover portion to position the gas sensor in the interstitial space.

In some embodiments, the structure is a valve or a joint.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
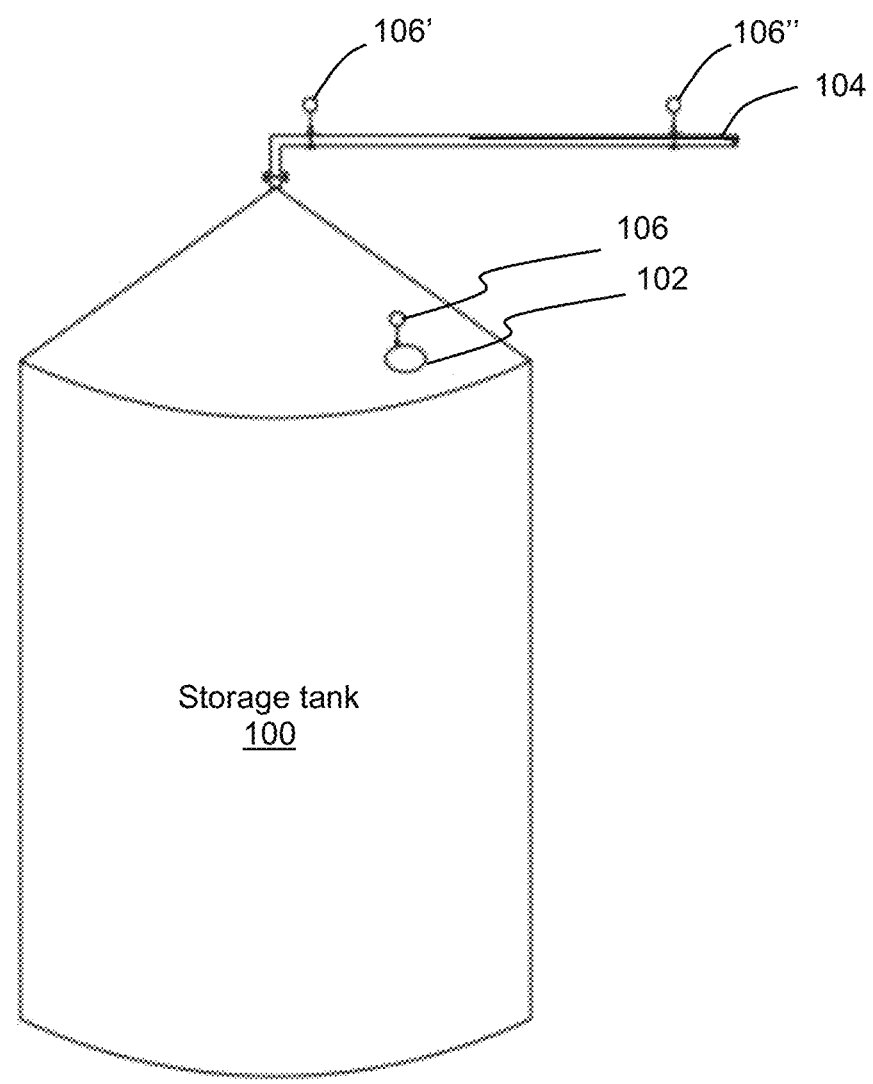
FIG. 1 illustrates a storage tank and a plurality of gas detection devices in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Embodiments described herein provide novel systems, devices, and methods for at least monitoring locations that may experience unwanted emissions of materials such as gasses. These embodiments may be implemented in various types of facilities and with different types of equipment.

The embodiments herein may help ensure compliance in applications such as spill prevention, control, and countermeasure implementation; leak detection and repair; or the like. 40 C.F.R. § 60, for example, provides requirements regarding calibrating equipment, obtaining gas samples, and generating reports. The embodiments herein may assist facilities in satisfying these types of requirements, such as by providing verified reports of gas detection, generating incident reports, scheduling investigative visits, or the like.

The systems, devices, and methods herein therefore reduce the need for human intervention. Additionally, the near-instantaneous detection and reporting of gas enables unwanted leaks or emissions to be addressed quickly and efficiently.

FIG. 1 illustrates a storage tank 100 with a thief hatch 102 in accordance with one embodiment. Thief hatches such as thief hatch 102 are commonly used on tanks such as those used for storing oil. Thief hatches may be used as pressure relief devices and for sampling a tank's contents. A gas collection line 104 may extend from the storage tank 100.

Also shown in FIG. 1 are gas detection devices 106, 106', and 106" of the described embodiments. Gas detection device 106 may be operably connected to or otherwise in proximity to the thief hatch 102. This positioning enables the gas detection device 106 to detect gas emitting from or near the thief hatch 102.

Gas detection device 106' may be positioned near the joint of the storage tank 100 and the gas collection line 104. The gas detection device 106' may be located here to detect gas emitting from the joint of these components, which may be susceptible to leaks. For example, these components may not be properly positioned with respect to each other to create a proper seal therebetween.

Gas detection device 106" may be positioned further downstream on the gas collection line 104. For example, the gas detection device 106" may be positioned in proximity to pipe joints or fittings (e.g., where two or more pipe segments connect) to detect gas emitting at these locations.

Figure 2:
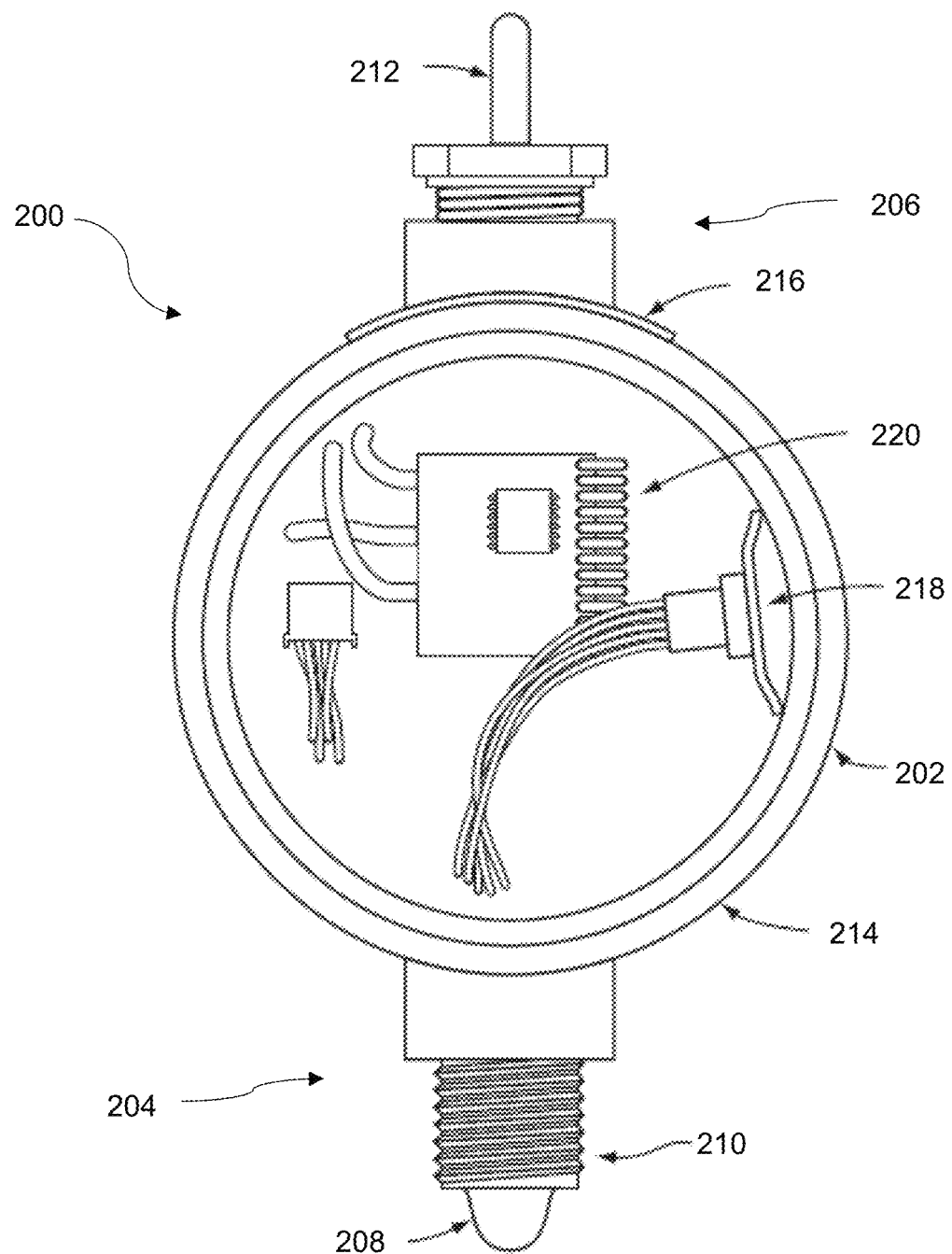
FIG. 2 illustrates a gas detection device in accordance with one embodiment.

The gas detection device described herein may include a housing portion configured with at least one gas sensor, one or more processors executing instructions stored on memory to process data from the at least one gas sensor, and a communication device configured to transmit a signal regarding the processed data. The housing portion may be formed of a material that is rated for the environment. For example, the housing portion may be subject to hazardous gasses or other material and must be designed to withstand such exposure FIG. 2 illustrates a gas detection device 200 in accordance with one embodiment. The gas detection device 200 may include a housing 202 graded to operate in a hazardous location. The housing 202 may include a first end 204 and a second end 206. The first end 204 may include one or more gas sensors 208 that can be positioned to detect gas emitting from a structure. For example, the gas sensor 208 may be a methane sensor to detect methane emitting from a structure such as the tank 100 of FIG. 1.

The type of gas sensor 208 may vary and may depend on the application. The type of gas sensor 208 may depend on the gas or other type of substance associated with a structure.

The first end 204 may also include a threaded portion 210 to connect the gas detection device 200 to a thief hatch cover or other location or structure. Although the first end 204 is configured with a threaded portion, other connection mechanisms or components may be used to operably connect the gas detection device 200 to a structure, which may be similarly configured to receive the first end 204.

For example, the connection between the first end 204 and a structure may be a press-fit connection, a spring-loaded connection, a pin-and-lock connection, a hook-and-loop connection, a magnetic connection, or the like. These are only examples, and other types of coupling means, whether available now or invented hereafter, may be used to operably position the gas detection device 200 with respect to a structure.

The second end 206 may be configured with at least one antenna 212. The antenna 212 may receive instructions for the gas detection device 200 and communicate data regarding the detection of gas. The antenna 212 may transmit signals to one or more remote monitoring systems or centers indicating that the gas sensor 208 has detected gas.

The gas detection device 200 may also be configured with one or more battery devices 214 for supplying power to various components of the gas detection device 200. The battery(ies) 214 may be configured as part of or on the housing 202, and may be replaced as necessary or charged by one or more photovoltaic cells 216. Additionally, or alternatively, the battery(ies) 214 may be equipped with a hard-wire connection to a production site's electrical power system.

The gas detection device 200 may also include an analog-to-digital (ADC) interface 218 for converting an analog signal received from the gas sensor 208 to a digital signal for one or more processors 220. The processor(s) 220 may perform any processing steps on the received data before transmittal by the antenna 212.

Figure 3:
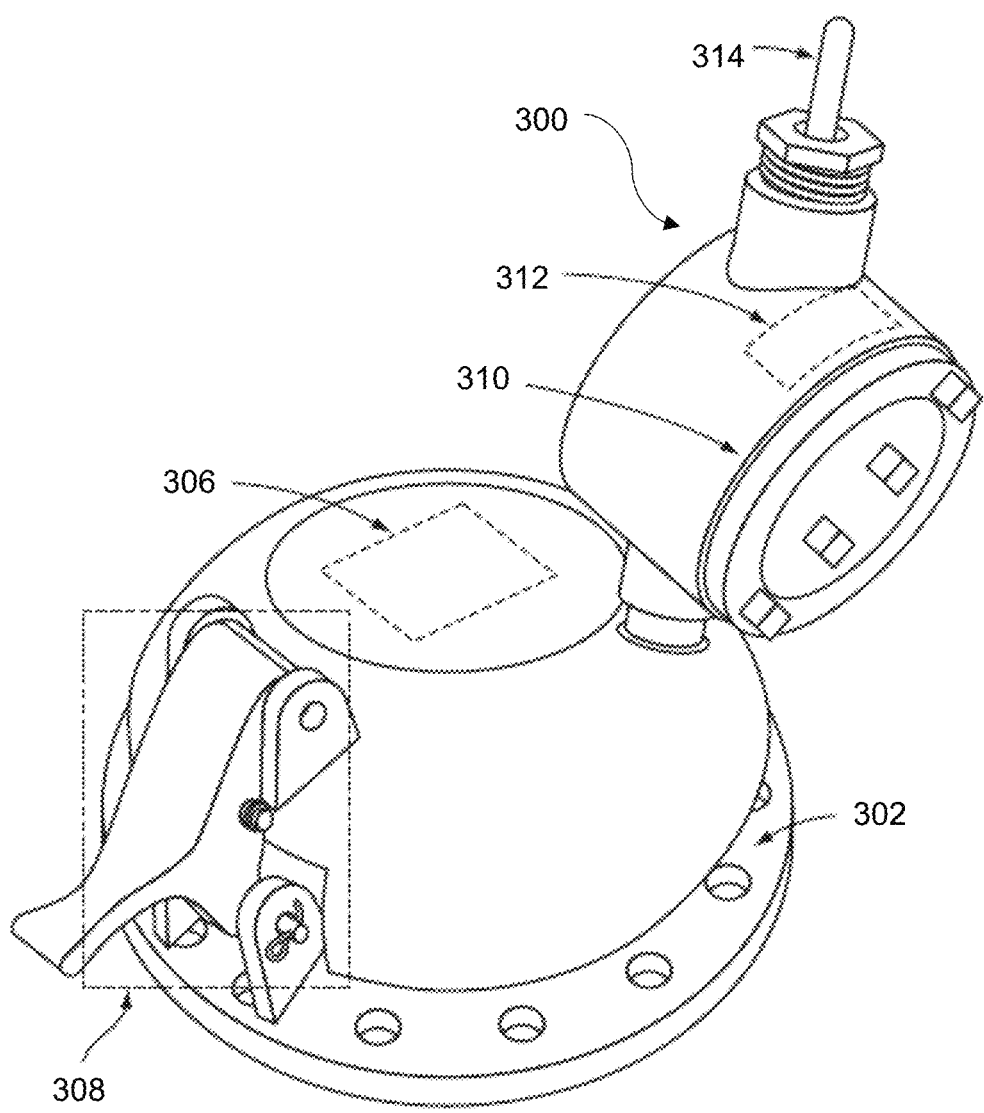
FIG. 3 illustrates a gas detection device operably connected with a thief hatch in accordance with one embodiment.

FIG. 3 illustrates a gas detection device 300 operably connected to a thief hatch 302 in accordance with one embodiment. The thief hatch 302 may also include one or more photovoltaic cells 306, and may also be configured with a limit switch 308 to detect whether the thief hatch 302 is closed. As seen in FIG. 2, the gas detection device 300 may include a housing 310 configured with the sensor(s) and related components, one or more photovoltaic cells 312, and an antenna 314.

In this embodiment, the gas detection device 300 may have been inserted into an aperture in the thief hatch 302. For example, the gas detection device 300 may be configured with a series of threads, to engage a series of threats on the thief hatch 302.

Figure 4:
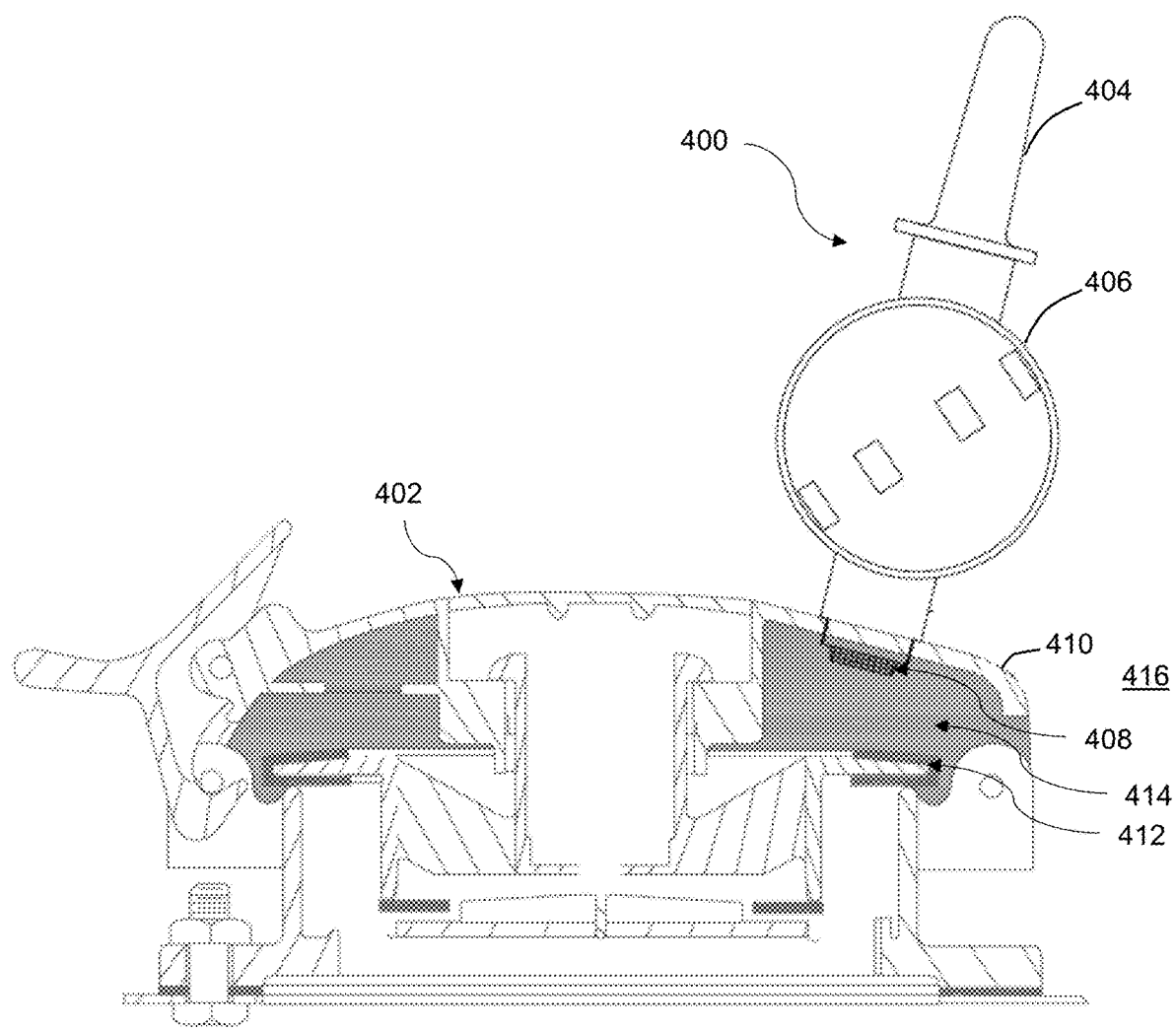
FIG. 4 illustrates a cross-sectional view of a gas detection device operably connected with a thief hatch in accordance with one embodiment.

FIG. 4 illustrates a cross-sectional view of a gas detection device 400 operably connected to a thief hatch 402 in accordance with one embodiment. The gas detection device 400 and the thief hatch 402 may be similar to the gas detection device 300 and thief hatch 302, respectively, of FIG. 3.

As seen in FIG. 4, the gas detection device 400 is operably connected to the thief hatch 402, and is illustrated as including an antenna 404 and a housing portion 406. The gas detection device 400 may be connected to the thief hatch 402 via any suitable connection component(s) such as, but not limited to, a threaded coupling, a press fit, a spring-lock, etc.

Other types of connection component(s), whether available now or invented hereafter, may be used as long as the gas detection device 400 can be operably connected to the thief hatch 402 or other type of structure to accomplish the objectives of the embodiments herein. Regardless of the connection component, the gas sensor 408 of the gas detection device 400 should be positioned to detect gas emitted from or within the thief hatch 402.

For example, the thief hatch 402 includes a cover 410, a seal 412, and an interstitial space 414 formed between the cover 410 and the seal 412. As seen in FIG. 4, the gas sensor 408 extends into the interstitial space 414 to detect gas therein. The interstitial space 414 may also be exposed to the ambient environment 416. Under normal operations, there should not be a detectable amount of gas in the interstitial space 414. Accordingly, if the gas sensor 408 detects gas in the interstitial space 414, it may be a cause for concern that should be remedied or at least investigated.

Figure 5:
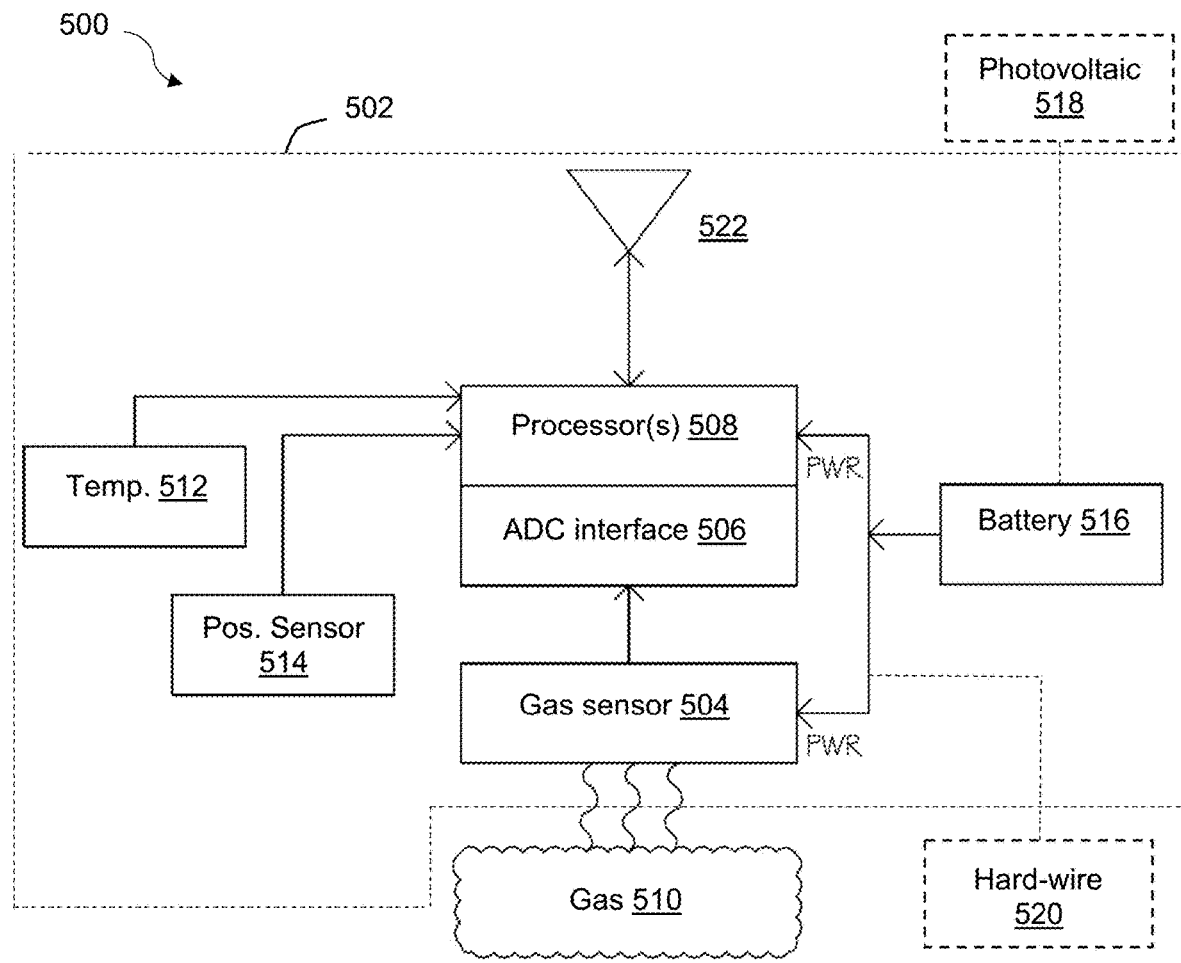
FIG. 5 presents a diagram of a gas detection device in accordance with one embodiment.

FIG. 5 presents a diagram of a gas detection device 500 in accordance with one embodiment. The gas detection device 500 may be similar to the gas detection devices of any one of FIGS. 1-4. The diagram shows a plurality of components within a housing 502. These components may include a gas sensor 504 that is in operable connectivity with an ADC interface 506 and one or more processors 508 executing instructions stored on memory.

The ADC interface 506 may act as an intermediary between the gas sensor 504 and the processor(s) 508. Specifically, upon detecting a gas 510, the gas sensor 504 may produce an analog signal indicative of said gas detection and communicate the signal to the ADC interface 506. The ADC interface 506 may then convert that signal to a digital signal that is processable by the processor(s) 508.

The processor(s) 508 may be any hardware device capable of executing instructions stored on memory to provide various subsystems, components, or modules. The processor(s) 508 may include a microprocessor, a field programmable gate array (FPGA), an application-specific integrated circuit (ASIC), or other similar devices. In some embodiments, such as those relying on one or more ASICs, the functionality described as being provided in part via software may instead be configured into the design of the ASICs and, as such, the associated software may be omitted.

The memory may be L1, L2, L3 cache, or RAM memory configurations. The memory may include non-volatile memory such as flash memory, EPROM, EEPROM, ROM, and PROM, or volatile memory such as static or dynamic RAM, as discussed above. The exact configuration/type of memory may of course vary as long as instructions for operating the gas detection device can be executed.

The processor(s) 508 may receive data or otherwise be in communication with a various other sensors, components, or modules. For example, the gas detection device 500 may include one or more temperature sensors 512 for gathering temperature data. This may include temperature of the ambient environment, temperature of the housing 502, temperature of detected gas, or some combination thereof.

The processor(s) 508 may also issue control instructions to the components of the gas detection device. For example, the processor(s) 508 may configure the gas sensor 504 to activate periodically. Rather than always having the gas sensor 504 active, the processor(s) 508 may activate the gas sensor 504 at intervals (e.g., once a minute) to determine the presence or absence of a gas. The time period between each gas sensor 504 reading may be adjusted based on the desired or required speed of gas detection, accuracy of gas detection, and battery life.

The position sensor 514 may provide data regarding the position of the structure or gas detection device 500. For example, if the structure is a thief hatch, the position sensor 514 may be in communication with a sensor that detects if the thief hatch is closed. In these embodiments, the thief hatch may be configured with a contact or limit switch and communicate to the position sensor 514 a signal if the thief hatch remains open for some period of time. As another example, the position sensor 514 may include one or more gyroscopes or accelerometers that detect the orientation of the gas detection device 500. For example, if the gas detection device 500 is connected to a thief hatch as in FIG. 3 or 4, the orientation of the gas detection device 500 may indicate whether the thief hatch is open or closed.

The processor(s) 508, as well as other components of the gas detection device 500, may receive power from one or more batteries 516. The battery(ies) 516 may be replaced or recharged by a photovoltaic cell 518 as needed. One or more photovoltaic cells 518 may be added to the exterior of the housing 502, thief hatch, or other structure.

Additionally or alternatively, components of the gas detection device 500 may be powered via a hard-wired connection 520 to a power source external to the gas detection device 500. For example, a gas detection device 500 may be equipped with a hard-wired power connection to a production site's electrical power system.

The above-described components of the gas detection device 500 are exemplary, and other components in addition to or in lieu of those mentioned above may be used in conjunction with the gas detection devices described herein. For example, the gas detection device may be configured with one or more imagery gathering devices for gathering imagery of a structure (e.g., to determine if there is noticeable, physical damage).

The processor(s) 508 may include one or more wireless communications modules such as BLUETOOTH®, ZigBee, or the like, may be in operable connectivity with an antenna 522. The antenna 522 may communicate with other communications equipment such as those associated with remote monitoring systems. An administrator at these locations may be notified of the gas detection and take appropriate remedial action The gas detection device in accordance with the described embodiments may be operably connected to a structure such as a thief hatch of a tank to detect gas emitted therefrom. The gas detection device may similarly be attached to or in proximity to other structures such as pipes, valves, fittings, joints, or the like. The gas detection device may also include or otherwise be configured with a connection component to operably position the housing portion with respect to a structure to enable the at least one gas sensor to detect a gas emitting from the structure. While the gas detection devices described herein may be connected directly to a structure from which gas is to be detected, the gas detection devices may instead be connected to other structures (e.g., walls, floors, ceilings), as long as they are able to detect gas emitted from some other structure.

Figure 6:
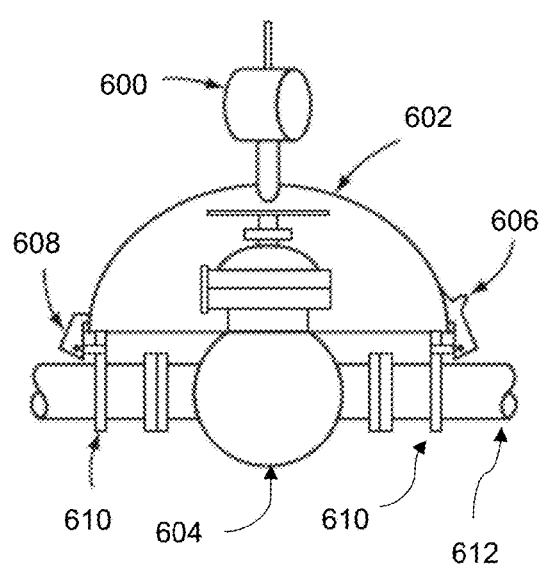
FIG. 6 illustrates a gas detection device operably connected to a structure in accordance with one embodiment.

Although the present application is largely discussed in the context of thief hatches, the gas detection device of the embodiments herein may be operably positioned with respect to other structures. FIG. 6 illustrates a gas detection device 600 configured with an interstitial cover 602 in accordance with one embodiment. The interstitial cover 602 is illustrated as translucent, and is positioned over a valve assembly 604. The interstitial cover 602 may include hinge 606 and latch 608 to attach the cover 602 to one or more mounting brackets 610. The mounting brackets 610 may be configured with piping system 612 for transporting the gas. In this configuration, the gas detection device 600 may detect gas within the interstitial cover 602, such as due to leaks at or in proximity to the valve assembly 604.

Figure 7:
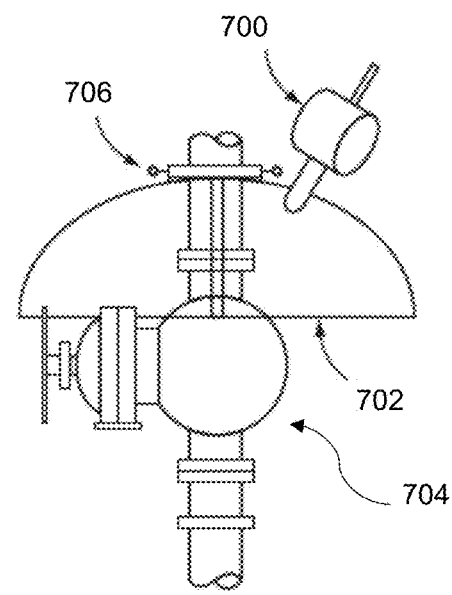
FIG. 7 illustrates a gas detection device operably connected to a structure in accordance with another embodiment.

FIG. 7 illustrates another embodiment, and shows a gas detection device 700 configured with an interstitial cover 702 that is mounted in proximity to a valve assembly 704. In this embodiment, the interstitial cover 702 may be positioned over the valve assembly 706 by one or more mounting collars 706. The gas detection device 700 may detect gas within the interstitial cover 702, such as due to leaks at or in proximity to the valve assembly 704.

Figure 8:
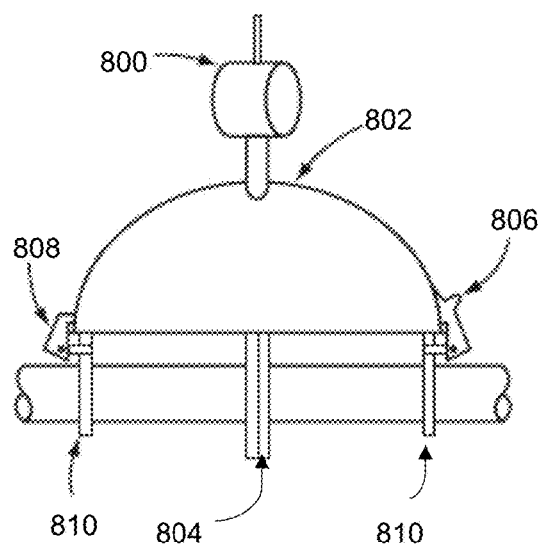
FIG. 8 illustrates a gas detection device operably connected to a structure in accordance with another embodiment.

FIG. 8 illustrates another embodiment, and shows a gas detection device 800 configured with an interstitial cover 802 that is mounted over a joint 804. In this embodiment, the interstitial cover 802 may be positioned over the joint 804 by hinge 806 and latch 808 portions that attach to mounting brackets 810. The gas detection device 800 may detect gas within the interstitial cover 802, such as due to leaks at or in proximity to the joint 804.

Figure 9:
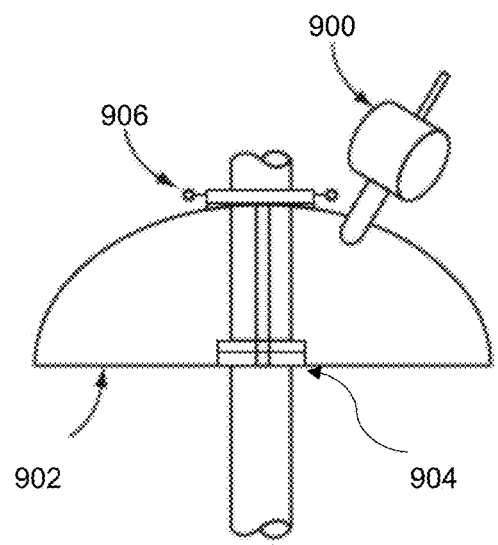
FIG. 9 illustrates a gas detection device operably connected to a structure in accordance with another embodiment.

FIG. 9 illustrates another embodiment, and shows a gas detection device 900 configured with an interstitial cover 902 that is mounted over a joint 904. In this embodiment, the interstitial cover 902 may be positioned over the joint 904 by a mounting collar 906. The gas detection device 900 may detect gas within the interstitial cover 902, such as due to leaks at or in proximity to the joint 904.

Figure 10:
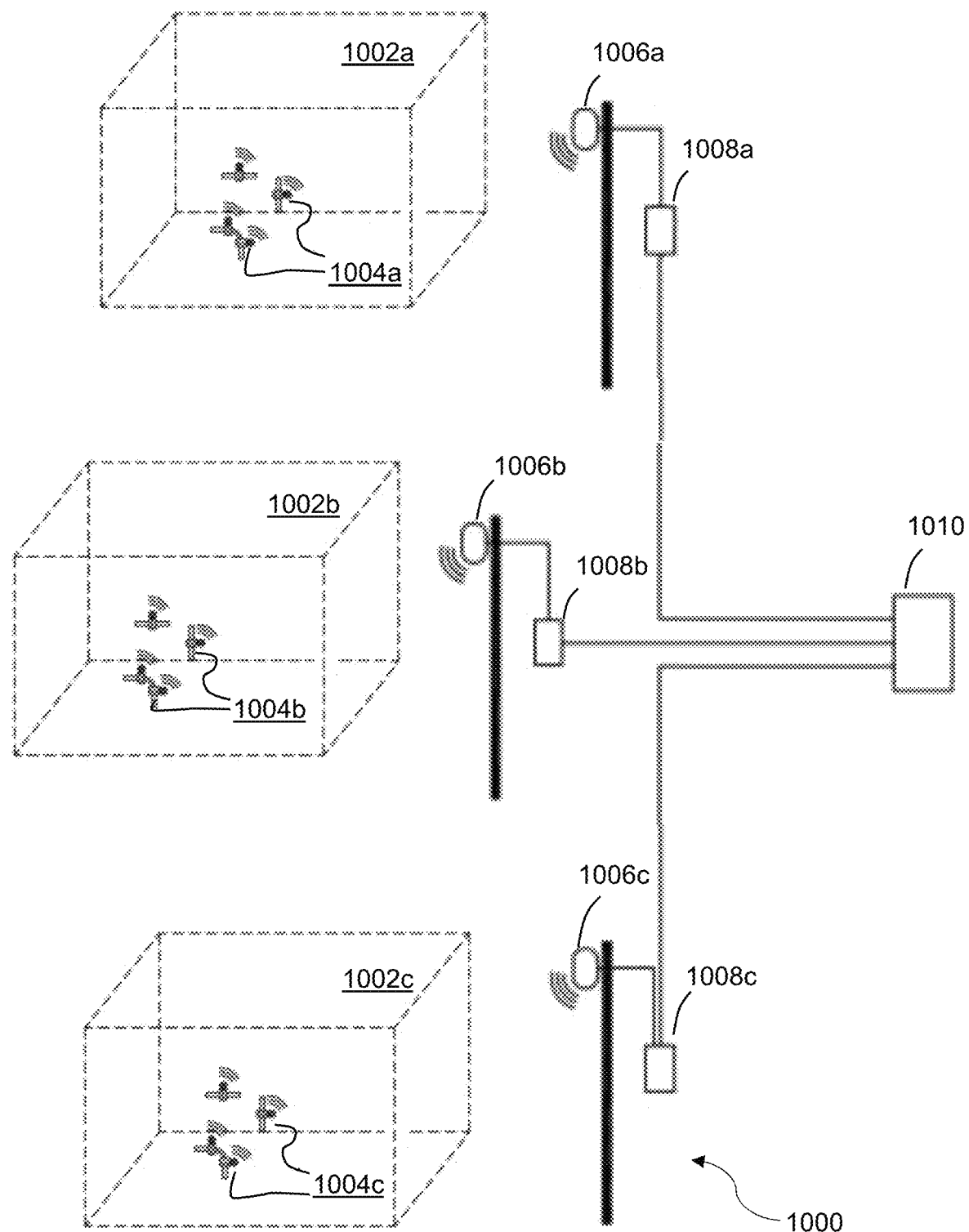
FIG. 10 illustrates a gas detection system in accordance with one embodiment.

FIG. 10 illustrates a gas detection system 1000 in accordance with one embodiment. The system 1000 may include a plurality of zones 1002a—c that may each be associated with a work site. Each zone 1002a—c may have one or more gas detection devices 1004a—c for detecting gas at their respective zone. That is, gas detection device(s) 1004a may be located at zone 1002a, gas detection device(s) 1004b may be located at zone 1002b, and gas detection device(s) 1004c may be located at zone 1002c. Each gas detection device 1004a—c may be operably connected to or in proximity to a structure within each zone as discussed previously.

Each zone 1002a—c may also include or otherwise be associated with a telecommunications device 1006a—c, respectively. The telecommunications devices 1006a—c may receive data from gas detection devices 1004a—c in their respective zones 1002a—c. The telecommunications devices 1006a—c may be configured as a radio frequency (RF) communications module and may be further configured to, via communication links 1008a—c, communicate with a remote monitoring system 1010.

The remote monitoring system 1010 receives from deployed gas detection devices data for further analysis, storage, presentation to an administrator via a user interface, or the like. The remote monitoring system 1010 may also provide instructions to one or more gas detection devices. For example, the remote monitoring system 1010 may provide instructions regarding how frequently a gas detection device should be activated. If structures or equipment in a certain zone 1002a—c are older than other equipment and therefore more likely to experience leaks, the remote monitoring system 1010 may instruct the gas detection devices associated with those structures to remain activated or to activate more frequently than other gas detection devices. Similarly, if a zone is located in proximity to a school or other populous location, the gas detection device(s) associated with that zone may be activated more frequently than others. These rules may be provided by an administrator or generated autonomously by the remote monitoring system 1010. For example, the remote monitoring system 1010 may consider location data (e.g., provided by GPS-based sensors associated with the gas detection device(s)) in providing instructions to the gas detection devices.

The remote monitoring system 1010 may also be in communication with other structures or components in each zone. For example, if gas is detected in an undesirable location, the remote monitoring system 1010 may close valves near that location to prevent further gas from being emitted.

The remote monitoring system 1010 may also be in communication with one or more user devices. The user device(s) may be configured as, for example, a mobile device, a table, a PC, a desktop, a smartwatch, or the like. Upon receiving a signal that a gas detection device has detected gas, the user device(s) may present an alert to an administrator. The alert may be a visual-based alert, an audio-based alert, a haptic-based alert, or some combination thereof. An administrator may view parameters associated with an alert, such as where the gas was detected. An administrator may then issue a work task for the location at which the gas was detected to be inspected, repaired, or the like. Additionally, or alternatively, the remote monitoring system 1010 may autonomously generate a work task regarding the gas detection. For example, the remote monitoring system may generate a report populated with data tags such as the location of the gas detection, an identifier of the gas detection device that detected the gas, the type of gas detected, an amount (e.g., a concentration) of a gas detected, a risk level associated with the gas detection, or the like.

Figure 11:
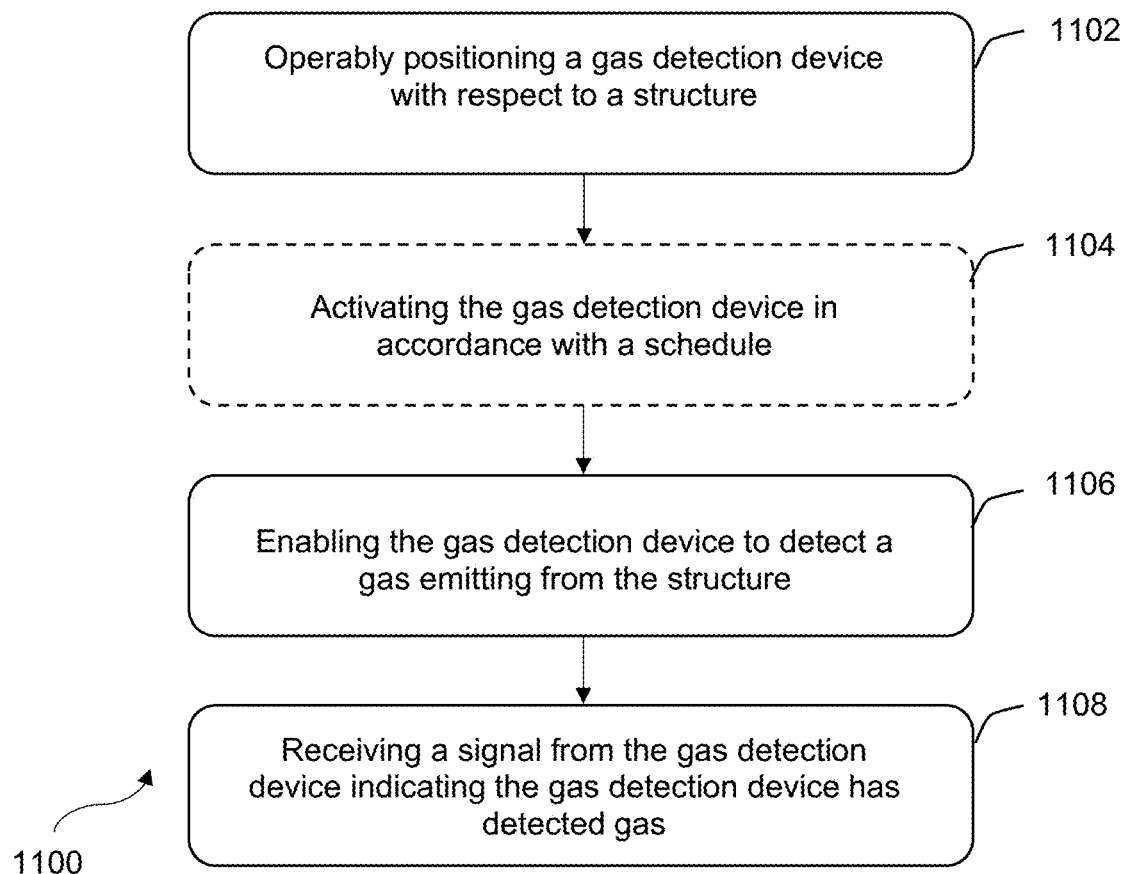
FIG. 11 depicts a flowchart of a method for detecting gas in accordance with one embodiment.

FIG. 11 depicts a flowchart of a method 1100 for detecting gas in accordance with one embodiment. Step 1102 involves operably positioning a gas detection device with respect to a structure. The gas detection device may be similar to the gas detection devices of any one of FIGS. 1-10, for example. The structure may be associated with a thief hatch, a valve, a joint, piping, or any other structure such that the gas detection device is able to detect gas to accomplish the objectives of the embodiments herein.

Step 1104 may be optional and involves activating the gas detection device in accordance with a schedule. It may not be desirable or necessary for a gas detection device to always be activated. Accordingly, method 1100 may involve instructing or configuring the gas detection device to be activated periodically, such as once a minute. The schedule in which a gas detection device is activated may depend on the structure, the location of the gas detection device, or the like.

Step 1106 involves enabling the gas detection device to detect a gas emitting from the structure. The gas detection device or sensor may be activated for a period of time sufficient to detect gas and generate a signal indicating that it has detected gas.

Step 1108 involves receiving a signal from the gas detection device indicating the gas detection device has detected gas. This signal may be received at a monitoring system such as the remote monitoring system 1010 of FIG. 10. The remote monitoring system 1010 may also be in communication with one or more databases for storing data regarding operational history of one or more gas detection devices. For example, the database(s) may store records of when a gas detection device detected gas, the location of the gas detection device, the quantity of the gas detected, the time of the gas detection, whether the gas detection was remedied, etc.

Although the present application largely discusses systems, methods, and devices for detecting gas, the embodiments herein may be applied in other applications and for different purposes. For example, sensor(s) used in conjunction with the detection device may be configured to detect liquids or solids that emit from a structure.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A gas detection device comprising:
    a housing portion configured with:
        at least one gas sensor,
        one or more processors executing instructions stored on memory to process data from the at least one gas sensor, and
        a communication device configured to transmit a signal regarding the processed data; and
    a connection component to operably position the housing portion with respect to a structure to enable the at least one gas sensor to detect a gas emitting from the structure, wherein the structure is a thief hatch including:
        a cover portion,
        a seal, and
        an interstitial space between the cover portion and the seal, wherein the connection component is configured to be operably connected with the cover portion to position the at least one gas sensor in the interstitial space.

2. The gas detection device of claim 1 wherein the one or more processors are configured to periodically activate the at least one gas sensor to detect the gas emitting from the structure.

3. The gas detection device of claim 2 wherein the one or more processors are configured to periodically activate the at least one gas sensor in accordance with a schedule.

4. The gas detection device of claim 1 further comprising a position detection sensor to detect the thief hatch is open, and the transmitted signal indicates the thief hatch is open.

5. The gas detection device of claim 1 wherein the transmitted signal includes at least one of location data pertaining to the location of the detected gas, timing data regarding the time of the detection, or quantity of the gas detected.

6. The gas detection device of claim 1 further comprising:
    a mounting collar configured to removably attach to the structure.

7. The gas detection device of claim 1 further comprising a position detection sensor to detect position of the structure.

8. The gas detection device of claim 1 wherein the signal is transmitted over a narrow bandwidth Internet-of-Things (IoT) connection.

9. The gas detection device of claim 1 further comprising a location detection device to gather data regarding location of the gas detection device.

10. A gas detection system comprising:
    a first gas detection device in accordance with claim 1, wherein the first gas detection device is located at a first site;
    a first communications module positioned at the first site and configured to communicate with the first gas detection device; and
    a remote monitoring system configured to receive data regarding the first gas detection device from the first communications module and issue instructions regarding the first gas detection device to the first communications module.

11. The system of claim 10 further comprising:
    a second gas detection device in accordance with claim 1, wherein the second gas detection device is located at a second site; and a second communications module positioned at the second site and configured to communicate with the second gas detection device;

wherein the remote monitoring system is further configured to receive data regarding the second gas detection device from the second communications module and issue instructions regarding the second gas detection device to the second communications module.

12. A method for detecting gas, the method comprising:

operably positioning the gas detection device of claim 1 with respect to the structure; and enabling the gas detection device to detect a gas emitting from the structure.

13. The method of claim 12 further comprising receiving a signal from the gas detection device indicating the gas detection device has detected gas.

14. The method of claim 13 wherein the received signal includes at least one of location data pertaining to the location of the detected gas, timing data regarding the time of the gas detection, or quantity of the gas detected.

15. The method of claim 13 wherein the signal is transmitted over a narrow bandwidth Internet-of-Things (IoT) connection.

16. The method of claim 12 further comprising activating the gas detection device in accordance with a schedule.

* * * * *